(12) United States Patent
Maas

(10) Patent No.: US 11,654,238 B2
(45) Date of Patent: May 23, 2023

(54) DEVICE FOR EXTRACTING A FLUID FROM AN AMPOULE

(71) Applicant: Eurotrol B.V., Ede (NL)

(72) Inventor: Bartholomeus Henricus Antonius Maas, Ede (NL)

(73) Assignee: Eurotrol B.V., Ede (NL)

( * ) Notice: Subject to any disclaimer, the term of this patent is extended or adjusted under 35 U.S.C. 154(b) by 377 days.

(21) Appl. No.: 16/756,488

(22) PCT Filed: Oct. 29, 2018

(86) PCT No.: PCT/EP2018/079543
§ 371 (c)(1),
(2) Date: Apr. 16, 2020

(87) PCT Pub. No.: WO2019/086368
PCT Pub. Date: May 9, 2019

(65) Prior Publication Data
US 2020/0330687 A1     Oct. 22, 2020

(30) Foreign Application Priority Data
Oct. 30, 2017   (EP) ..................... 17199154

(51) Int. Cl.
*A61M 5/28*      (2006.01)
*A61M 5/31*      (2006.01)
*A61M 5/315*     (2006.01)

(52) U.S. Cl.
CPC ............ *A61M 5/283* (2013.01); *A61M 5/285* (2013.01); *A61M 5/3145* (2013.01); *A61M 5/31505* (2013.01); *A61M 5/31513* (2013.01)

(58) Field of Classification Search
CPC .... A61M 5/283; A61M 5/285; A61M 5/2429; A61M 5/2422; A61M 5/2425;
(Continued)

(56) References Cited

U.S. PATENT DOCUMENTS 1,770,631 A * 7/1930 Smith ................. A61M 5/2429
604/203
4,596,561 A * 6/1986 Meyer ................. A61M 5/2429
604/190
(Continued)

FOREIGN PATENT DOCUMENTS

EP    0264273    4/1988
GB    1376843    12/1974
(Continued)

*Primary Examiner* — Katherine H Schwiker
*Assistant Examiner* — Hong-Van N Trinh
(74) *Attorney, Agent, or Firm* — N.V. Nederlandsch Octrooibureau

(57) ABSTRACT

A device for extracting a fluid from an ampoule, comprising a plunger body (2) arranged for enclosing an ampoule (3), and a syringe body (4) movable relative to the plunger body (2). The syringe body (4) comprises a piston member (6) and an outer tubular casing (8) concentrically arranged around the piston member (6). The piston member (6) comprises an insertion end (10), receivable within the plunger body (2) and arranged for insertion in the ampoule (3), an ejection end (12) attached to the outer tubular casing (8), and a lumen (14) extending between the insertion end (10) and the ejection end (12). The plunger body (2) and the syringe body (4) form an actuating arrangement of the device (1) arranged to move the piston member (6) through the ampoule (3) during operation and forcing a fluid from the ampoule (3) through the lumen (14).

14 Claims, 2 Drawing Sheets

Figure 1:
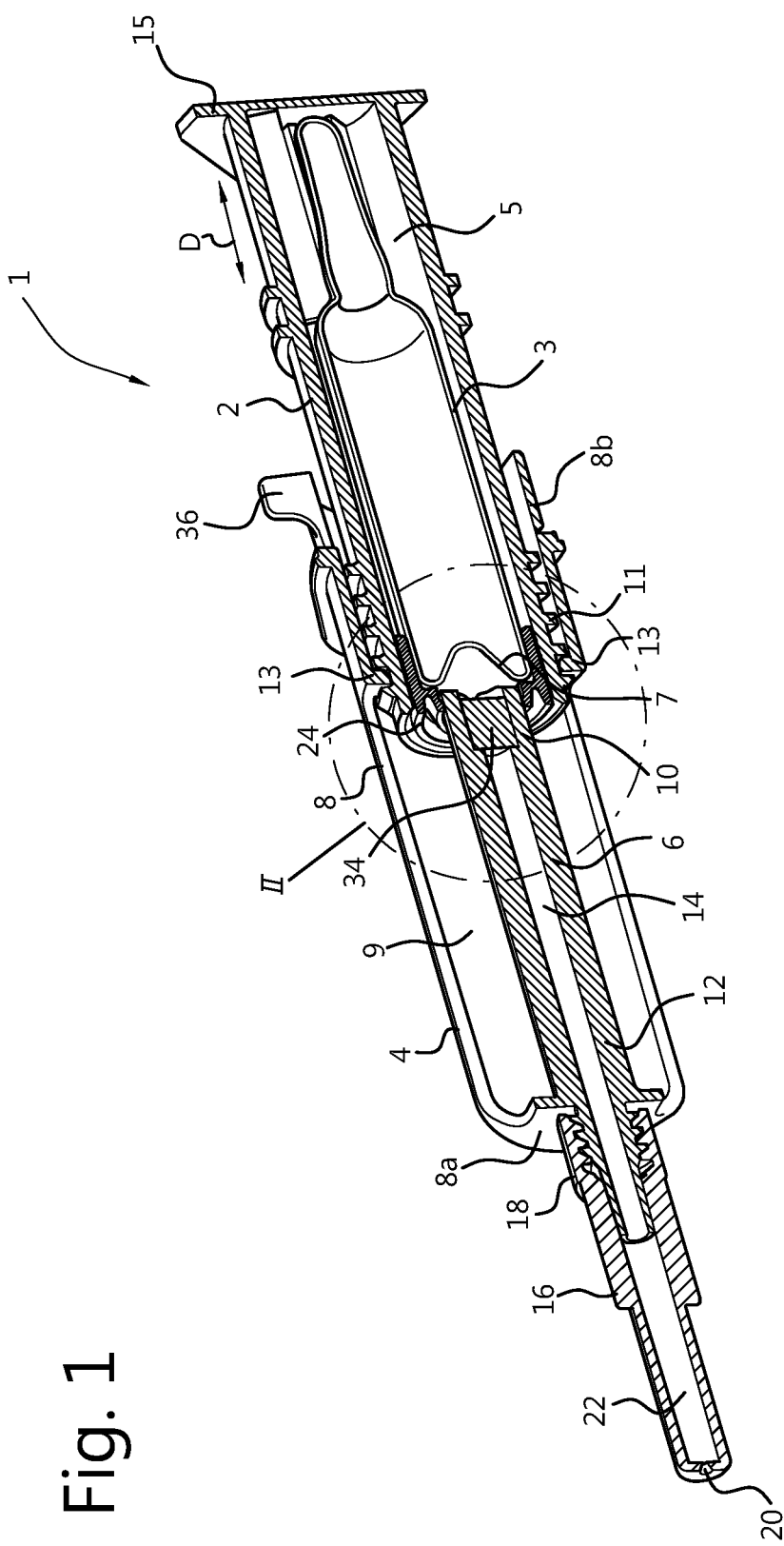

(58) Field of Classification Search
CPC .......... A61M 5/2466; A61M 2005/247; A61M 2005/2474; A61M 5/281; A61M 5/288; A61M 5/3145; A61M 5/31505; A61M 5/31513; A61M 5/31511; A61M 5/282
See application file for complete search history.

(56) References Cited

U.S. PATENT DOCUMENTS

| | | |
|---|---|---|
| 2005/0137532 A1 | 6/2005 | Rolla |
| 2007/0225656 A1 | 9/2007 | Hoyle, Jr. |
| 2013/0345631 A1 | 12/2013 | Plouvier et al. |
| 2017/0281868 A1* | 10/2017 | Roedle ................ A61M 5/2429 |

FOREIGN PATENT DOCUMENTS

| | | | |
|---|---|---|---|
| WO | 9218178 | 10/1992 | |
| WO | 0100261 | 1/2001 | |
| WO | WO-0100261 A1 * | 1/2001 | ........ A61M 5/31596 |

* cited by examiner

DEVICE FOR EXTRACTING A FLUID FROM AN AMPOULE

FIELD OF THE INVENTION

The present invention relates to a device for extracting a fluid from an ampoule, such as a disposable glass, plastic or metal ampoule.

BACKGROUND ART

American patent publication U.S. Pat. No. 6,099,510 describes a device for withdrawing a liquid from a sealed glass ampoule. The device includes a frame holding the sealed glass ampoule in upright or slightly inclined position, such that a tip of the ampoule points upwardly. An element is provided which presses against tip portion of the ampoule in order to break the tip of the ampoule in the region of the neck thereof. The device further includes a withdrawing element to be introduced into the glass ampoule in an area between the bottom of the ampoule and the surface of the liquid therein, and which includes a cannula for withdrawing the liquid.

American patent publication U.S. Pat. No. 5,628,353 discloses a method and system for drawing a liquid from a sealed glass ampoule. The ampoule is held in a support in upright position with the ampoule bottom facing upwards, and the bottom is destroyed mechanically by inserting a withdrawing element. The liquid content of the ampoule is sucked from a splinter-free zone of the glass ampoule.

International patent application WO2017/021949 describes a syringe for direct use with medical ampoules and vials. The syringe comprises a syringe barrel and a syringe plunger having an open end and hollow interior volume for receiving a medicine containing portion of a broken/opened ampoule. An ampoule interface element is configured for deployment between an outer surface of the ampoule and a surface of the hollow interior volume so as to hold the medical ampoule in the hollow interior volume. In use, medicine contained in the already opened ampoule is drawn into the syringe barrel through a passageway in the syringe plunger by vacuum pressure which is created when the syringe plunger is drawn out of the syringe barrel.

American patent publication U.S. Pat. No. 4,596,561 discloses a pre-filled single dose syringe, having a barrel, a nozzle and a needle carrying ferrule. A shaft provided with a stoppering device acts as a piston member.

International patent publication WO01/00261 discloses a liquid transfer device for transfer of medication from a prefilled medication container. A piston is provided on a plunger to slidingly and sealingly engage a barrel of the device.

SUMMARY OF THE INVENTION

The present invention seeks to provide a device for extracting a sample fluid from an ampoule, such as a disposable glass, plastic or metal ampoule, wherein the device allows the ampoule both to be opened safely in a sealed environment provided by the device and subsequently emptied in an efficient manner whilst preventing contamination of the fluid contained in the ampoule.

According to the present invention, a device of the type defined in the preamble above is provided comprising a syringe body, and a plunger body arranged for enclosing an ampoule, wherein the plunger body is movable relative to the syringe body. The syringe body comprises a piston member and an outer tubular casing concentrically arranged around the piston member. The piston member is provided with an insertion end which is receivable within the plunger body and arranged for insertion in the ampoule. The piston member is further provided with an ejection end attached or connected to the outer tubular casing and a lumen or passageway extending between the insertion end and the ejection end. The plunger body and the syringe body of the device form a cooperative actuating arrangement configured to move the piston member through the interior of the ampoule during operation, forcing a sample fluid from the ampoule through the lumen.

The present invention embodiments allow a safe and reliable opening of an ampoule, and subsequently providing a fluid from the ampoule without risk of any contamination of the fluid. Furthermore, the user of the device is also protected from hazards normally involved in using ampoules, such as personal injury by cutting fingers on sharp edges after breaking a top from an ampoule.

SHORT DESCRIPTION OF DRAWINGS

Figure 2:
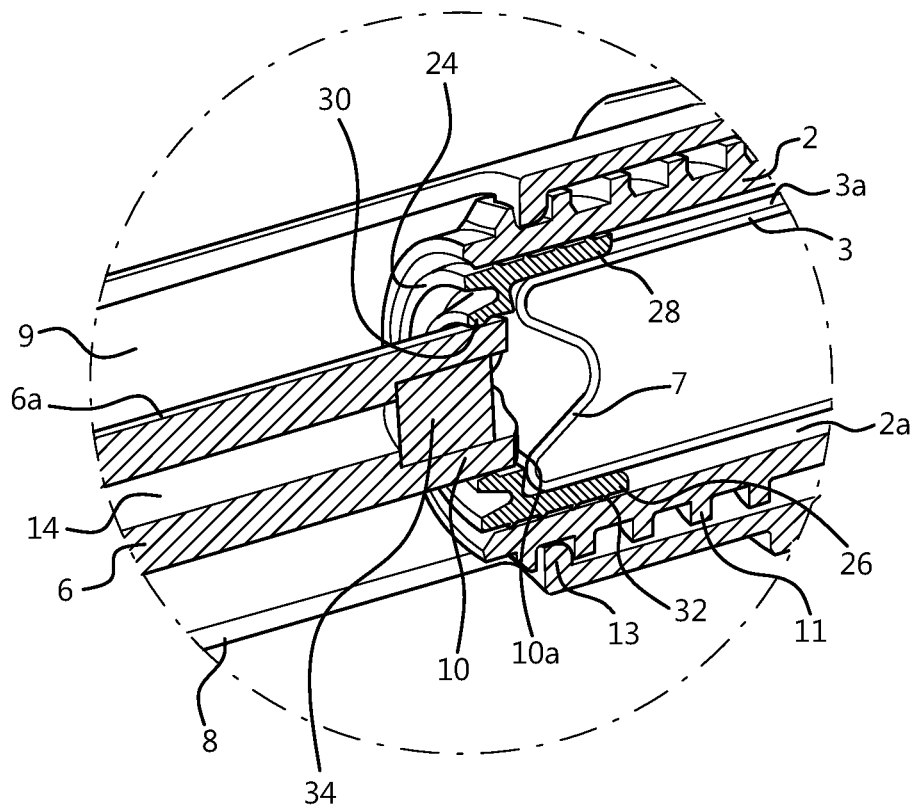
Figure 3:
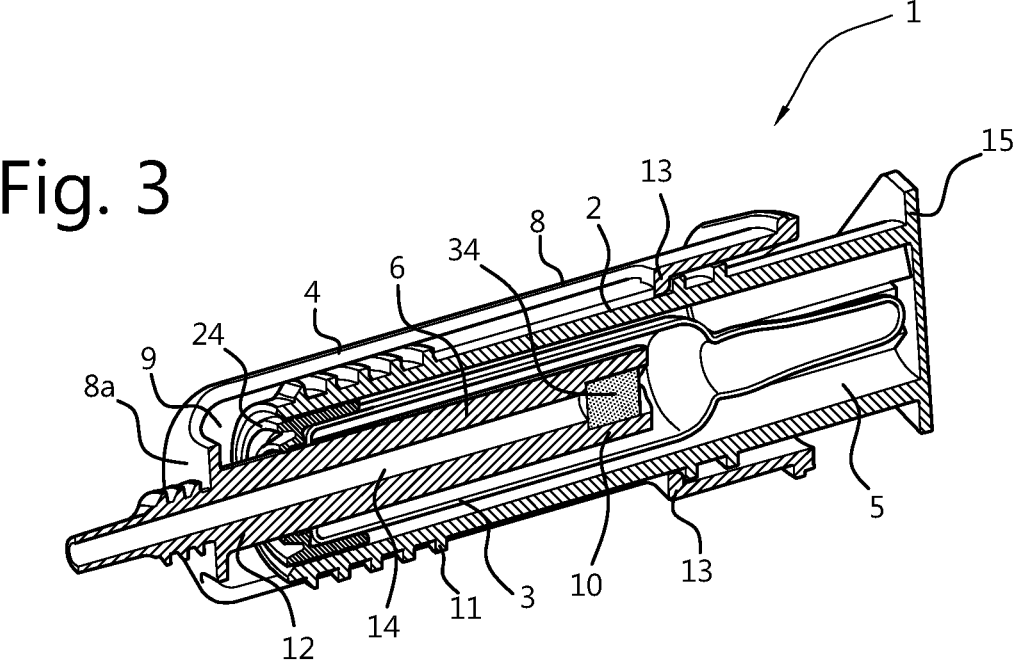

The present invention will be discussed in more detail below, with reference to the attached drawings, in which FIG. 1 shows a three dimensional cross sectional view of a device according to an embodiment of the present invention;

FIG. 2 shows a partial cross sectional view of the device according to an embodiment of the present invention; and FIG. 3 shows a cross sectional view of a further embodiment of the present invention device in a position where the ampoule has been emptied.

DESCRIPTION OF EMBODIMENTS

The present invention embodiments can be applied in quality control applications, such as testing and/or calibrating measurement equipment. FIG. 1 shows a three dimensional cross sectional view of a device 1 for extracting a fluid from an ampoule according to an embodiment of the present invention. In FIG. 1 a syringe like device 1 is depicted capable of receiving an ampoule 3 or hermetically sealed vial 3 containing a sample, such as a fluid. The ampoule 3 may be a disposable ampoule made of glass, plastic, or a metal such as aluminium. As used herein the term ampoule 3 is to be understood as any type of a fluid container, such as an ampoule, a vial or a carpule. The ampoule 3 may typically contain a chemical or a pharmaceuticals fluid that must remain protected from various contaminants, air intrusion etc., e.g. to be used for testing and/or calibrating a medical instrument at a point of service or at a point of care. The device 1 comprises a syringe body 4 and a plunger body 2 arranged for enclosing the ampoule 3 and movable relative to the syringe body 4. The plunger body 2 provides a protective environment or enclosure for the ampoule 3 such that, e.g., external impact of the ampoule 3 can be avoided. The syringe body 4 is provided with an elongated piston member 6 and an outer tubular casing 8 (or housing) concentrically arranged around the piston member 6. The concentric arrangement of the outer tubular casing 8 and the piston member 6 provides an elongated annular cavity 9 within which the plunger body 2 is receivable and is able to move there through in a linear fashion in direction "D" as shown, e.g. by exerting a (torqueing) force or pressure on a handling part 15 of the plunger body 2. As shown, the plunger body 2 may be embodied as a cylindrical body receivable within the annular cavity 9.

In an embodiment, the piston member 6 and the outer tubular casing 8 of the syringe body 4 may be separate elements, wherein the piston member 6 may be connected to the outer tubular casing 8 in a releasable fashion, e.g. by means of a threaded or snap-fit connection. In an alternative embodiment the piston member 6 and the outer tubular casing 8 from a unitary arrangement, which may be manufactured as a single piece by e.g. compression or injection moulding.

In an advantageous embodiment, both the syringe body 4 and the plunger body 2 are made of a plastic material, e.g. suitable for injection moulding techniques. To allow visibility of the liquid in the device 1 (and in the ampoule 3), the syringe body 4, the plunger body 2, or both the syringe body 4 and plunger body 2 may be (partially) made of a transparent material. It is noted the material and/or structure of the plunger body 2 may be selected to allow heat exchange between the ampoule 3 and the environment during actual use of the device 1 (cooling and/or heating). This may be accomplished by selecting a material having a high thermal conductivity, or by providing one or more apertures in the (wall of the) plunger body 2.

The piston member 6 comprises an insertion end 10 to be received within the plunger body 2 and arranged for insertion into the interior of the ampoule 3. In an exemplary embodiment the insertion end 10 is receivable within a storage space 5 of the plunger body 2 used to accommodate the ampoule 3 and configured to provide a protective enclosure. The piston member 6 is further provided with an ejection end 12 opposite to the insertion end 10, wherein the ejection end 12 is attached or connected to the outer tubular casing 8, e.g. to a base portion 8a thereof. The piston member 6 further comprises a lumen 14 (or passageway) extending between the insertion end 10 and the ejection end 12 allowing the content of the ampoule 3 to be transported there through.

The plunger body 2 and the syringe body 4 form a cooperative actuating arrangement of the device 1 which is configured to move the piston member 6 through the ampoule 3 during operation and to force a fluid from the ampoule 3 through the lumen 14 toward the ejection end 12.

According to the present invention, the plunger body 2 is arranged to be moved into the annular cavity 9 toward the base portion 8a of the outer tubular casing 8, by exerting a force or pressure on the handling part 15 of the plunger body 2. In doing so the piston member 6 is forced through a wall part or bottom part 7 of the ampoule 3 and subsequently forces or urges the sample fluid contained in the ampoule 3 through the lumen 14 to the ejection end 12 as it moves deeper into the interior of the ampoule 3 (positive displacement action). The wall part 7 of the ampoule 3 is e.g. prepared to break in a controlled manner once pressure is applied by the insertion end 10 of the piston member 6, by special shape of the wall part 7 or additional features such as a printed breaking line. More general, the wall part 7 may be mechanically, thermally or chemically treated to provide a localised weakening of the ampoule 3 at area of the wall part 7. E.g. the wall part 7 may be scored (cutting of a ring using a diamond cutting tool), chemically etched or laser cut. Once the plunger body 2 has been inserted in the annular cavity 9 to a maximum insertion depth thereof, the plunger body 2 may be retracted from the annular cavity 9 back to a configuration as depicted in FIG. 1. In a group of embodiments, the device 1 further comprises a container part 16 with an attachment portion 18 connectable to the ejection end 12 of the piston member 6. The container part 16 is configured to allow flushing of the lumen 14 and to allow the ejection end 12 to be completely filled with the sample fluid from the ampoule 3 without contamination. In an exemplary embodiment the container part 16 comprises an aperture 20 opposite to the attachment portion 18, allowing air or fluid to be removed from the lumen 14 and container part 16 before the sample fluid is ejected from the device 1.

In an embodiment, the container part 16 comprises a container lumen 22, which may be embodied as an elongated passageway similar in diameter to an inner diameter of the lumen 14. In a further embodiment, the container part 16 comprises storage chamber 22 having an inner diameter substantially larger than an inner diameter of the lumen 14.

In an exemplary embodiment the attachment portion 18 comprises a male or female Luer type connecting portion to be cooperatively connected to a corresponding Luer type connecting portion of the ejection end 12 or the base portion 8a of the outer tubular casing 8. In an alternative exemplary embodiment the attachment portion 18 is in threaded engagement with the ejection end 12 or the base portion 8a of the outer tubular casing 8. Each of the Luer and threaded type connection of the attachment portion 18 to the ejection end 12 provides a reliable sealed connection preventing leakage of the sample fluid from the device 1.

According to the present invention, a new and unopened ampoule 3 can thus be opened safely within the device 1 followed by ejection the sample fluid. The embodiment shown in FIG. 1 and described above allows both opening and emptying of the ampoule 3 through a two-stage process. FIG. 3 shows a cross sectional view of a further embodiment of the present invention device 1 (embodiment without the container part 16) in a position where the ampoule 3 has been emptied. The first stage representing controlled opening of the ampoule 3 in the protective storage space 5 of the plunger body 2 through threaded engagement between the syringe body 4 and the plunger body 2. The second stage represents ejection of the sample fluid from the ampoule 3 once the ampoule 3 has been opened/pierced by the insertion end 10 and ejection of the sample fluid can commence through sliding engagement, i.e. linear sliding engagement, between the plunger body 2 and the syringe body 4.

A particular advantage of the device 1 is that a new and unopened ampoule 3 can be stored within the plunger body 2 of the device 1 and subsequently opened and emptied through a linear displacement of the plunger body 2 into the tubular outer casing 8, i.e. the annular cavity 9. There is absolutely no need to break or open the ampoule 3 outside of the device 1 and then storing the opened ampoule into the device 1. On the contrary, the device 1 of the present invention explicitly avoids having to break or open the ampoule 3 outside of the device 1 so that any chance of possible contamination and/or air intrusion of the sample fluid contained in the ampoule 3 is minimized. Instead, the plunger body 2 is configured to provide a protective environment for an unopened ampoule 3 and to allow opening and emptying of the ampoule 3 within the device 1 itself. The quality of the sample fluid contained within the ampoule 3 can be preserved and maintained by the device 1 as much as possible, so that ejected fluid from the ampoule 3 is free from contaminants (e.g. caused by air intrusion). Furthermore, the present invention embodiments also provide an improved safety for users of ampoules 3, as no breaking action is needed which might result in personal injury of the user or by-standers (cutting by sharp (glass) edges, glass fragments being inhaled or entering the eye, etc.).

It is noted that when using conventional type of glass ampoules 3 in combination with the present invention device 1 embodiments, it is no longer needed to break the top part of the ampoule 3 (at its neck) to obtain access to the fluid inside the ampoule 3. This has an added advantage that ampoules 3 can be used which are almost completely filled with fluid (no unused volume inside the ampoule 3), as the access to the fluid is provided from the wall part 7 of the ampoule 3.

Safety wise and to guarantee that the device 1 has not yet been used for opening and emptying an ampoule 3, an embodiment is provided wherein the plunger body 2 or the syringe body 4 comprises a releasable locking member 36 configured to prohibit displacement of the plunger body 2 relative to the syringe body 4. The locking member 36 may also be advantageously used as tamper proof device. In this embodiment the ampoule 3 can only be emptied by using the device 1 after removing the locking member 36. In the FIG. 1 embodiment, the securing member 36 is implemented as a circumferential rim portion 8b of the outer tubular casing 8 configured for being teared therefrom, e.g. with a locking assembly preventing mutual movement of plunger body 2 and syringe body 4. Once the locking member 36 has been released, the plunger body 2 is no longer immobilized relative to the syringe body 4 and the plunger body 2 is moveable into the annular cavity 9 for opening the ampoule 3 and ejecting the sample fluid.

In an advantageous embodiment, the actuating arrangement formed by the plunger body 2 and the syringe body 4 comprises a sliding arrangement between the plunger body 2 and the syringe body 4, wherein the sliding arrangement permits sliding contact or engagement between the plunger body 2 and the syringe body 4. In this embodiment the plunger body 2 is able to slide through the outer tubular casing 8 in e.g. telescopic fashion and allows for varying displacement speeds of the plunger body 2 through the annular cavity 9, depending on forces applied for moving the plunger body 2. By sliding the plunger body 2 through the outer tubular casing 8 the fluid from the ampoule 3 can be slowly or quickly ejected from the device 1 as the piston member 6 moves through the ampoule 3.

Before actual ejection of the sample fluid is possible, a new or sealed ampoule 3 residing or stored within the plunger body 2, i.e. the storage space 5, will need to be opened first. For that purpose an embodiment is provided wherein the actuating arrangement formed by the plunger body 2 and the syringe body 4 comprises a threaded arrangement between the plunger body 2 and the syringe body 4, wherein the threaded arrangement permits threaded engagement between the plunger body 2 and the syringe body 4. In this embodiment the threaded arrangement allows a better controlled mutual displacement of the plunger body 2 with respect to the syringe body 4, and hence a better controlled piercing of the wall part 7 by the insertion end 10 of the piston member 6 through rotation of the piston body 2 relative to the syringe body 4. The threaded engagement can be configured to provide a relatively slow but forceful displacement of the plunger body 2 with respect to the syringe body 4 through relative ease of rotation of the plunger body 2, as compared to a direct linear movement action for piercing the wall part 7.

As depicted in FIG. 1, threaded engagement between the plunger body 2 and the syringe body 4 may be achieved by an external thread 11 arranged on the plunger body 2 wherein the external thread 11 is in cooperative engagement with an internal protrusion 13 of the outer tubular casing 8. Conversely, in another embodiment it is conceivable that the outer tubular casing 8 comprises an internal thread in cooperative engagement with an external protrusion on the plunger body 2.

Both of the above mentioned sliding and threaded arrangement embodiments can be combined as shown in the embodiment of FIG. 1, providing a particularly convenient and effective device 1 for opening a new or unopened ampoule 3 and to subsequently eject a sample fluid therefrom.

As an example of operation of the device 1, initially the plunger body 2 and the syringe body 4 are in threaded engagement in an extended configuration of the device 1 as depicted in FIG. 1 using an external thread 11 on the plunger body 2 cooperating with an internal protrusion 13 of the outer tubular casing 8. Note that the extended configuration corresponds to the plunger body 2 being at a minimum insertion depth into the outer tubular casing 8, i.e. the internal cavity 9. At this minimum insertion depth the threaded engagement ensues. Then assuming an ampoule 3 is enclosed by the plunger body 2, rotation of the handling part 15 of the plunger body 2 allows it to be displaced/moved into the annular cavity 9 up to a point at which the insertion end 10 of the piston member 6 abuts the wall part or bottom part 7 of the ampoule 3. At this abutment point further rotation of the plunger body 2 allows the insertion 10 to pierce through or breach the wall part 7 in a controlled manner. Advantageously, the threaded engagement actually prevents shock wise movement of the plunger body 2 into the internal cavity 9 as the insertion end 10 pierces through the wall part 7, so that sudden or shock wise ejection of the sample fluid from the ampoule 3 is avoided. Through further rotation the insertion end 10 moves farther into the interior of the ampoule 3 and as a result the sample fluid is ejected from the ejection end 12.

Now, at some position of the insertion end 10 within the ampoule 3, the threaded engagement ends as the external thread 11 on the plunger body 2 only spans a limited length along the plunger body 2, thus wherein the length of the external thread 11 is considerably smaller than a maximum insertion depth of the plunger body 2 into the internal cavity 9. Once the external thread 11 no longer engages the internal protrusion 13, the plunger body 2 need not be rotated anymore, allowing it to freely slide farther into the internal cavity 9. So at this point the sliding engagement ensues as the threaded engagement terminates, wherein the plunger body 2 can be moved into the internal cavity 9 up to a collapsed configuration of the device 1, i.e. wherein the plunger body 2 is further inserted toward a maximum insertion depth of the internal cavity 9.

From the above it is readily understood that the threaded engagement also implies a form of sliding engagement between the plunger body 2 and syringe body 4, but it should be noted that this is achieved through rotation of the plunger body 2. However, the sliding arrangement and engagement referred to above is to be construed as not requiring rotation of the plunger body 2.

To aid a user in easily and properly dispensing a fixed amount of fluid from the device 1, the plunger body 2 is e.g. provided with measure lines. Alternatively or additionally, the combination of plunger body 2 and syringe body 4 may be provided with mechanical detents (providing a tactile feedback for a predetermined amount of fluid ejected from the device 1). In case of the rotary implementation as described above, the dimensions of the various parts (e.g. the pitch of the threaded engagement) may be chosen to provide a standard amount of ejected fluid for every full rotation.

As mentioned earlier, the plunger body 2 provides a protective enclosure for the ampoule 3 to prevent damaging it through e.g. external impact during storage and transport but also to minimize internal contamination of the device 1.

To further improve sealed engagement between the ampoule 3 and the device 1, reference is made to FIG. 2, showing a partial cross sectional view of an embodiment of the present invention device 1, and especially of a sealing member 24 thereof. In particular, to further improve sealed engagement between the ampoule 3 and the device 1, an embodiment is provided wherein the device 1 further comprises a sealing member 24 having a first sealing surface 26 in sealing engagement with an inner surface 2a of the plunger body 2. The sealing member 24 further comprises a second sealing surface 28 configured for sealing engagement with an outer surface 3a of the ampoule 3 and a third sealing surface 30 is provided in sealing engagement with an outer surface 6a of the piston member 6.

The sealing member 24 provides a "triplet" of sealing surfaces 26, 28 30 configured for simultaneous sealing engagement with the ampoule 3, the plunger body 2 and the piston member 6, wherein these sealing surfaces prevent contamination of the fluid sample contained in the ampoule 3 during operation. Furthermore, the sealing surfaces 26, 28, 30 prevent leakage and facilitate ejection of the fluid sample from the ampoule 3.

In an advantageous embodiment, the sealing member 24 comprises one or more circumferential ridges 32 provided on the first, second and/or the third sealing surface 26, 28, 30. The circumferential ridges 32 do not only provide additional sealing engagement but also increase frictional engagement where needed to facilitate positioning the sealing member 24 within the device 1. E.g., in the embodiment of the sealing member 24 as depicted in FIG. 2, the first sealing surface 26 is provided with one or more circumferential ridges 32 in sealing engagement with the inner surface 2a of the plunger body 2. The circumferential ridges 32 further increase fictional engagement between the sealing member 24 and the plunger body 2 such that the sealing member 24 exhibits a tighter fit within the plunger body 2. Such a tighter fit facilitates stationary positioning of the sealing member 24 when the outer surface 6a of the piston member 6 moves along the third sealing surface 30. The sealing member 24 is also advantageous for assembly of the device 1. The storage space 5 of the plunger body 2 has an internal wall conformal to an outer shape of the ampoule 3 (and can vary depending on the specific type of ampoule 3 to be used). Assembly can thus simply start with holding the plunger body 2 upright, and inserting the ampoule 3. The sealing member 24 can be applied to the bottom part of the ampoule 3 before insertion into the plunger body 2, or after the ampoule 3 has been inserted into the plunger body 2. Then, the syringe body 4 is attached to the plunger body 2 in the extended position (e.g. using the securing member 36 to lock the device 1 in its storage configuration). The container part 16 is then attached to the ejection end 12 of the piston member 6, or already attached to the syringe body 4 before mating to the plunger body 2.

During or before assembly of the device 1, it is possible to use sterilized parts (such as ampoule 3, plunger body 2, sealing member 24, piston member 6) or to sterilize these parts just before assembly. This allows to provide a fluid using the device for various applications requiring sterility, without any chance of compromising the degree of sterility.

In an alternative embodiment the handling part 15 of the plunger body 2 comprises a release cap member for accessing the storage space 5, allowing an ampoule 3 to be inserted or removed from the plunger body 2. As an alternative embodiment, the release cap may be implemented as a flip-cap arrangement, allowing easy handling of the combination of plunger body and release cap member. This group of embodiments would allow to easily insert an ampoule 3 into the device 1 in specific circumstances, and also to re-use the device 1 by exchanging an emptied ampoule 3 for a fresh ampoule 3, To use the device 1, a new or unopened ampoule 3 is provided and put in the storage space 5 by releasing and subsequently closing the cap member in the handling part 15. The cap member, or other part of the device 1, may be provided with a tamper proof seal component.

In an even further embodiment, the sealing member 24 and plunger body 2 are integrated in a single component, i.e. being of a unitary construction. The sealing member 24 can be integrated with the plunger body 2 e.g. using two component injection moulding techniques. This allows to have only a single component to be handled during assembly, yet still provides a sufficient sealing of the bottom part of the ampoule 3 in the plunger body 2 in operation.

In an embodiment, the insertion end 10 of the piston member 6 comprises a piercing portion 10a configured for piercing through a wall part 7 of the ampoule 3, such as a bottom part 7 of the ampoule 3. This embodiment allows an unopened ampoule 3 to be opened effectively within the device 1 by the insertion end 10 of the piston member 6. By moving the plunger body 2 into the outer tubular casing 8 the piercing portion 10a is urged through the wall part 7 of the ampoule 3. Further displacement of the plunger body 2 into the outer tubular casing 8 results in the insertion end 10 being moved deeper into the interior of the ampoule 3, forcing the sample fluid through the lumen 14.

To facilitate easier insertion of the insertion end 10 into the ampoule 3, an embodiment is provided wherein the piercing portion 10a comprises a staged or stepped diameter profile. Such a staged diameter profile can be configured to reduce forces needed for moving the plunger body 2 into the annular cavity 9 as the piercing portion 10a breaches the wall part 7 with ease. E.g., an embodiment may be provided wherein a first stage or step is provided comprising an outer diameter of the piercing portion 10a smaller than a major outer diameter of the piston member 6. Such a first stage concentrates push forces imposed by the insertion end 10 onto a localised portion of the wall part 7 of the ampoule 3. In a further embodiment it is conceivable that the piercing portion 10a comprises a first stage or step having an outer diameter of about 1-7 mm and a second stage/step having an outer diameter of about 7.1 to 11 mm, which would be typical for a 3 ml type of ampoule 3. If a smaller or larger type of ampoule 3 is used (e.g. 2, 5 or 10 ml), of course the values may be different, e.g. a first stage with an outer diameter of about 1-10 mm and a second stage with an outer diameter of about 11 to 14 mm. In this embodiment the first stage or step may be optimized to facilitate piercing the wall part 7 while the second stage or step may be optimized for positive fluid displacement from the ampoule 3. The second stage may also be implemented with a continuous increasing diameter (sloped wall). In an even further embodiment, the piercing portion 10a has a face with recesses surrounding the entrance of the lumen 14, which allows to effectively catch debris originating from the piercing action on the ampoule 3, and prevent possible blockage of the lumen 14.

Fluid displacement from the ampoule 3 through relative movement between the outer tubular casing 8 and the plunger body 2 can be improved through an embodiment wherein an outer diameter of the piston member 6 is substantially equal to or smaller than an internal major diameter of the ampoule 3. In this embodiment the piston member 6 can be configured to snugly fit into the interior of the ampoule 3 for minimizing leakage along the piston member 6 and an inner surface of the ampoule 3.

As mentioned above, the device 1 of the present invention can be used as a syringe like device, wherein, e.g. direct ejection of the fluid from the device 1 is required. This may be advantageous in point of care applications, where the device 1 is to be carried to a specific location outside of a (controlled) laboratory environment, such as homes and other remote locations, and used by non-trained persons.

An embodiment is provided wherein an internal diameter of the lumen 14 is less than a predetermined fraction (e.g. one third) of an internal major diameter of the ampoule 3. This embodiment minimizes an inner volume of the lumen 14, and the lumen 14 primarily serves to transport the fluid from the ampoule 3 toward the ejection end 12. Also, minimizing the inner volume of the lumen 14 reduces wasting fluid from the ampoule 3, which is advantageous for local point of service/direct injection purposes where maximum yield from the ampoule 3 is desired. In even further embodiments, the predetermined fraction is one half (still providing a relative small volume within lumen 14), or even as low as one fifth (providing an even smaller volume in lumen 14). In an exemplary embodiment, the inner diameter of the ampoule 3 is 11.75 mm (outer diameter of 12.75 mm and wall thickness of 0.5 mm) and the internal diameter of the lumen 14 is 3 mm. For various sizes of ampoules 3, the inner diameter may vary similar to the (standard) outer diameters: for a 1 and 2 ml ampoule 3 the standard outer diameter is 10.75 mm; for a 3 ml ampoule 12.75 mm, fora 5 ml ampoule 14.75 mm, fora 10 ml ampoule 17.75 mm and for 20, 25 and 30 ml ampoules 22.5 mm. It is noted that the wall thickness is about 0.5 mm but this may be higher for the higher volume ampoules 3. In this embodiment a needle member (not shown) may be connected to the ejection end 12 of the piston member 6 or the base portion 8a of the outer tubular casing 8.

In a further embodiment it is also conceivable that the ejection end 12 or the base portion 8a is configured to connect to another device which is to be provided with the fluid contained in the ampoule 3. E.g. in case of a measurement apparatus, the device 1 of the present invention may be used to provide a test or calibration fluid from the ampoule 3 directly to the measurement apparatus, wherein the ejection end 12 of the device 1 is connected to a fluid input port of the measurement apparatus.

In even further applications the device 1 of the present invention may be used as a sampling device from which a sample of fluid contained in the ampoule 3 can be retrieved by means of e.g. an external needle inserted into the lumen 14. So in this application the device 1 is not used for direct ejection therefrom but as a device from which the fluid in the ampoule 3 can be retrieved using e.g. a common syringe of which the needle is inserted into the lumen 14. Retracting the syringe plunger from the syringe barrel subsequently allows the fluid in the lumen 14 to be transferred into the common syringe. In light of such an application there is an embodiment wherein an internal diameter of the lumen 14 is larger than a predetermined fraction (e.g. one third) of an internal major diameter of the ampoule 3. This embodiment allows for a needle to be inserted into the lumen 14 for extracting a fluid from the device 1. In even further embodiments, the predetermined fraction is one half, or one fifth.

In contrast to prior art devices, the device 1 according to the present invention embodiment provides a solution to the undesired need of having to open the ampoule 3 in an open environment. Using the present invention device 1 contact between the sample fluid in the ampoule 3 and air and/or contaminants from the environment is prevented. To achieve this the plunger body 2 provides a protective enclosure/storage space 5 for the ampoule 3. By moving the plunger body 2 into the outer tubular casing 8, i.e. the annular cavity 9, the wall part 7 of the ampoule 3 is pierced/breached as the insertion end 10 is urged into the ampoule 3. While piercing the wall part 7, small wall fragments/debris such as glass, plastic or metal fragments may be left behind in the fluid contained in the ampoule 3. However, such wall fragments should not be transported through the lumen 14 as this would possibly cause (glass) splinters which might be harmful for the user or for an associated measuring device. To prevent wall fragments of the ampoule 3 to be ejected or retrieved from the device 1, an embodiment is provided wherein the lumen 14 comprises a filter member 34, blocking wall fragments and debris from being ejected (and ending up in e.g. a measurement apparatus where it can block or disturb sensitive sensors). Advantageously, the filter member 34 not only filters wall fragments/debris from the fluid, but it also allows for a greater volume of fluid to be displaced from the ampoule 3. In an embodiment, the insertion end 10 comprises a filter member 34, wherein the filter member 34 is arranged within the lumen 14 most proximal to the plunger body 2.

The embodiments of the present invention device 1 having a filter member 34 have an additional advantage when the ampoule 3 in combination with the device 1 are used in applications where a fluid is administered to a living human or animal, as it ensures that no possibly dangerous wall fragments and debris can enter the human/animal body.

The filter member 34 may be implemented in several structural variants, e.g. as a porous material filter, a felt or other web or sieve type of filter, a filter having a labyrinth structure of channels (e.g. a (multi-stage) closing lid on the piercing portion 10a of the insertion end 10 forming small channels at the edges of the closing lid), etc. The filter material may also be diverse, and e.g. includes but is not limited to polymer materials, metal materials. Structurally, the filter member 34 may be glued, welded or otherwise fixed to the insertion end 10.

The present invention has been described above with reference to a number of exemplary embodiments as shown in the drawings. Modifications and alternative implementations of some parts or elements are possible, and are included in the scope of protection as defined in the appended claims.

The invention claimed is:

1. A device for extracting a fluid from an ampoule, comprising
   a plunger body arranged for enclosing the ampoule, and a syringe body, the plunger body being movable relative to the syringe body, the syringe body having a piston member and an outer tubular casing arranged concentrically around the piston member,
   wherein the piston member comprises an insertion end receivable within the plunger body and arranged for insertion in the ampoule, an ejection end attached to the outer tubular casing, and a lumen extending between the insertion end and the ejection end,
   wherein the plunger body and the syringe body form an actuating arrangement of the device arranged to move the piston member through the ampoule during operation and forcing a fluid from the ampoule through the lumen, wherein the device further comprises
   a sealing member having a first sealing surface in sealing engagement with an inner surface of the plunger body, a second sealing surface configured for sealing engagement with an outer surface of the ampoule, and a third sealing surface in sealing engagement with an outer surface of the piston member during operation.

2. The device according to claim 1, wherein the device further comprises a container part with an attachment portion connectable to the ejection end of the piston member.

3. The device according to claim 2, wherein the container part comprises an aperture opposite to the attachment portion.

4. The device according to claim 1, the sealing member comprises one or more circumferential ridges provided on the first, second and/or the third sealing surface.

5. The device according to claim 1, wherein the insertion end of the piston member comprises a piercing portion for piercing through a wall portion of the ampoule.

6. The device according to claim 5, wherein the piercing portion comprises a staged diameter profile.

7. The device according to claim 1, wherein an outer diameter of the piston member is substantially equal to or smaller than an internal major diameter of the ampoule.

8. The device according to claim 1, wherein an internal diameter of the lumen is less than a predetermined fraction of an internal major diameter of the ampoule.

9. The device according to claim 1, wherein an internal diameter of the lumen is larger than a predetermined fraction of an internal major diameter of the ampoule.

10. The device according to claim 1, wherein the lumen comprises a filter member.

11. The device according to claim 1, wherein the actuating arrangement formed by the plunger body and the syringe body comprises a sliding arrangement between the plunger body and the syringe body.

12. The device according to claim 11, wherein the actuating arrangement formed by the plunger body and the syringe body further comprises a threaded arrangement between the plunger body and the syringe body.

13. The device according to claim 1, wherein the piston member and the outer tubular casing of the syringe body are separate elements.

14. The device according to claim 1, wherein the plunger body or the syringe body comprises a releasable securing member configured to prohibit displacement of the plunger body relative to the syringe body.

* * * * *